(12) United States Patent
Mustapha et al.

(10) Patent No.: US 10,362,666 B2
(45) Date of Patent: Jul. 23, 2019

(54) COMPAC CARBON ION LINAC

(71) Applicants: Brahim Mustapha, Naperville, IL (US); Alireza Nassiri, Woodridge, IL (US); Peter N. Ostroumov, Okemos, MI (US); Alexander S. Plastun, Okemos, MI (US); Aditya Goel, Downers Grove, IL (US)

(72) Inventors: Brahim Mustapha, Naperville, IL (US); Alireza Nassiri, Woodridge, IL (US); Peter N. Ostroumov, Okemos, MI (US); Alexander S. Plastun, Okemos, MI (US); Aditya Goel, Downers Grove, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 17 days.

(21) Appl. No.: 15/713,238

(22) Filed: Sep. 22, 2017

(65) Prior Publication Data

US 2018/0343733 A1 Nov. 29, 2018

Related U.S. Application Data

(60) Provisional application No. 62/511,253, filed on May 25, 2017.

(51) Int. Cl.
*A61N 5/10* (2006.01)
*H05H 7/22* (2006.01)
(Continued)

(52) U.S. Cl.
CPC ............... *H05H 7/22* (2013.01); *H05H 7/02* (2013.01); *H05H 7/04* (2013.01); *H05H 9/042* (2013.01);
(Continued)

(58) Field of Classification Search
None
See application file for complete search history.

(56) References Cited

U.S. PATENT DOCUMENTS

| 8,173,981 | B2 * | 5/2012 | Trbojevic | A61N 5/10 |
| | | | | 250/398 |
| 8,836,247 | B2 * | 9/2014 | Yamamoto | H05H 9/042 |
| | | | | 315/500 |
| 9,962,562 | B2 * | 5/2018 | Fahrig | A61N 5/1084 |
| 2004/0162457 | A1 * | 8/2004 | Maggiore | A61N 5/10 |
| | | | | 600/1 |
| 2007/0034812 | A1 * | 2/2007 | Ma | A61N 5/1031 |
| | | | | 250/492.21 |

(Continued)

*Primary Examiner* — Dion Ferguson
*Assistant Examiner* — Srinivas Sathiraju
(74) *Attorney, Agent, or Firm* — Cherskov Flaynik & Gurda, LLC

(57) ABSTRACT

The invention provides a method for accelerating protons and carbon ions up to 450 MeV/u in a very compact linac, the method comprising subjecting the particles to a radio frequency quadrupole field to accelerate the particles to at least 3 MeV/u, a drift tube linac (DTL) to an energy of 20 MeV/u, followed by a coupled DTL to 45 MeV/u and finally a high-gradient section made of CCL-type standing wave cavities or negative harmonic traveling wave cavities operating at S-band frequencies and capable of delivering voltage gradients of 40 to 60 MV/m. Focusing the accelerated particles while accelerated to higher energy is provided by appropriately placed constant field permanent magnets and electromagnetic quadrupoles. The compactness and power efficiency of the linac is enabled by using high-gradient structure in the S-band frequencies for lower energy particles than ever before. The low-intensity required for hadron therapy allows the use of small-aperture S-band structures and the operation at very high gradient compared to high-intensity machines for research. Operating with very short sub-microsecond pulses at repetition rates up to 400

(Continued)

US 10,362,666 B2

Page 2

Hz allows the fast and flexible beam energy and intensity tuning not provided by existing hadron therapy machines. The designed linac is capable of accelerating ions as heavy as neon to the full 450 MeV/u energy, therefore allowing fast beam switching if different ion sources are installed in the front-end of the linac.

18 Claims, 7 Drawing Sheets

(51) Int. Cl.
    *H05H 7/02*     (2006.01)
    *H05H 7/04*     (2006.01)
    *H05H 9/04*     (2006.01)

(52) U.S. Cl.
    CPC ............ H05H 9/044 (2013.01); H05H 9/045 (2013.01); *A61N 5/1043* (2013.01); *A61N 2005/1087* (2013.01); *H05H 2007/025* (2013.01); *H05H 2007/043* (2013.01); *H05H 2007/222* (2013.01); *H05H 2277/11* (2013.01)

(56) References Cited

U.S. PATENT DOCUMENTS

| | | | |
|---|---|---|---|
| 2010/0032580 A1* | 2/2010 | Caporaso | H01J 27/26 250/396 R |
| 2010/0038552 A1* | 2/2010 | Trbojevic | A61N 5/10 250/396 ML |
| 2010/0060207 A1* | 3/2010 | Caporaso | H01J 27/26 315/505 |
| 2010/0284502 A1* | 11/2010 | Piefer | G21G 1/10 376/190 |
| 2010/0320403 A1* | 12/2010 | Amaldi | A61N 5/10 250/492.3 |
| 2011/0096887 A1* | 4/2011 | Piefer | G21B 1/01 376/193 |
| 2012/0300890 A1* | 11/2012 | Piefer | G21G 1/08 376/158 |
| 2016/0353562 A1* | 12/2016 | Antaya | H01F 6/06 |
| 2017/0318657 A1* | 11/2017 | Aoki | H05H 7/001 |

* cited by examiner

COMPAC CARBON ION LINAC

PRIORITY

This utility patent application claims priority benefit as a Non-Provisional of U.S. Provisional Patent Application No. 62/511,253, filed on May 25, 2017, the entirety of which is incorporated herein by reference.

CONTRACTUAL ORIGIN OF THE INVENTION

The U.S. Government has rights in this invention pursuant to Contract No. DE-AC02-06CH11357 between the U.S. Department of Energy and UChicago Argonne, LLC, representing Argonne National Laboratory.

BACKGROUND OF THE INVENTION

1. Field of the Invention

This invention relates to LINACs and more specifically this invention relates to a compact system and method to accelerate particles toward a physiological target or a non-physiological target.

2. Background of the Invention

Ion beam therapy is becoming a standard of care for treatment of tumors. Approximately one third of the world's 15,000 accelerators are used for tumor therapy and other medical applications.

There are currently three technologies being used for radiation oncology: gamma/electron beams, proton beams, and carbon ion beams. The gamma/electron beam approach is by far the most mature and advances in techniques continue to improve its effectiveness. However, these particles spread the dose over the entire volume of a target tissue, thereby creating radiation damage to healthy parts.

Protons and carbon ions deposit most of their energy in a small depth, called the Bragg peak. Protons and gammas have the same radiobiological effectiveness (low linear energy transfer) so that the expected gains of proton therapy are restricted to the increased dose localization.

By contrast, carbon ions have a narrower Bragg peak than protons and also a higher biological effectiveness in the Bragg peak relative to that in the entrance region. Carbon ions deliver high linear energy transfer which makes them more effective at treating radiation resistant hypoxic tumors. In addition, carbon ions can deliver even more localized doses than protons due to their heavier mass and the resulting reduced transverse scattering.

Carbon therapy is a promising technique for cancer treatment, given its clinical efficiency and reduced toxicity profiles. This is because carbon ions could be better localized in the tumor volume. The ion deposits most of its energy by ionization in a very short distance just before it stops. The most efficient treatment is achieved when the energy deposition volume is changed in all three directions as fast as possible for treatment of moving organs.

430 MeV per nucleon carbon beam (MeV/u) is required to cover the full penetration depth that is up to about 30 cm (about 12 inches) of the human body. Three technologies are available for ion beam acceleration: cyclotrons, synchrotrons, and linear accelerators (LINACS).

Both cyclotrons and synchrotrons are expensive and bulky constructions with large magnets. A cyclotron is a continuous wave fixed energy machine. "Continuous wave" means it produces beam continuously in contrast to a pulsed machine that produces bursts or bunches of beam. Fixed energy means the beam cannot be produced at variable energy, only one energy at the exit of the cyclotron. It does not offer the flexibility of adjusting the time structure or the energy of the beam by simple tuning.

Energy adjustments in cyclotrons require degraders, which are variable thickness solid materials. This process generates a large amount of radiation and significantly worsens the beam quality. The effect is unnecessary beam loss and radiation that requires adequate shielding.

Synchrotrons are circular structures which require large magnets that consume large amounts of power. Indeed, some state of the art synchrotrons have a perimeter of about 70 meters. Due to the multi-turn acceleration in a synchrotron, changing the energy may take a few seconds such that it is not effective for fast three dimensional tumor painting or treatment of moving organs.

State of the art linacs require a large foot print at a Hospital or University Campus, with some linacs exceeding hundreds of meters in length.

A need exists in the art for a system and method for efficient ion therapy in oncology scenarios. The system and method should penetrate all aspects of a patient while minimizing exposure to healthy tissue. The system and method should have a small foot print so as to not impose on valuable real estate in hospital or oncology center settings. The system should also be a single pass system so as to be capable of changing the beam energy very quickly. This cannot be easily achieved in a synchrotron because of the multi-turn and cyclic nature of those machines.

SUMMARY OF INVENTION

An object of the invention is to provide a method and system for supplying ionic particle streams that overcomes many of the drawbacks of the prior art.

Another object of the invention is to provide a linear acceleration system and method for accelerating protons and many different ions (up to neon) to the same energy. A feature of the system is that the particles are accelerated to energies of about 400 MeV/u, wherein "u" is the nucleon. An advantage of the invented system and method is its application of ionic particle therapy to any region of the body.

Still another object of the invention is to provide a high efficiency linac. A feature of the invention is that it operates in the S-band frequency (e.g., frequencies around 3 GHz). An advantage of the invention is that this relatively higher frequency (compared to the lower frequencies of about 400 MHz of typical linacs) allows for higher voltage gradients and therefore shorter linacs. The invention enables therapeutic grade linacs with lengths of between about 30 and 50 meters; and typically 40 meters or less.

Yet another object of the present invention is to provide accelerating structures which cover velocity ranges from about 0.02 c to 0.8 c (where c is the speed of light). A feature of the invention is that it will provide 50 MV/m accelerating gradients. An advantage is the enablement of a 450 MeV/u accelerator for $^{12}C^{6+}$ ions and 250 MeV for protons, with a compact footprint of about 8 meters by 30-45 meters, compared to a 25 meter×25 meter footprint of state of the art configurations.

Another object of the present invention is to provide a linac as short as 40 meters. A feature of the invention is that pulsed S-band room-temperature structures are capable of delivering a voltage gradient between about 40 and about 60 MV/m. An advantage of the invention is that the pulsed nature allows fast change in beam energy which could be done pulse-per-pulse up to about 400 Hz. Energy modulated ion beam therapy is therefore enabled.

Still another object of the present invention is to provide a carbon ion linac operating in the S-band frequency. A feature of the invention is that the delivered carbon ion beam intensity is adjusted by changing the pulse repetition rate of the beam energy, and the pulse duration. An advantage of the invention is that the short beam pulses, at between approximately 100 and approximately 1000 nanoseconds (ns), reduces RF pulse length and the average RF power required for acceleration. This increases the RF breakdown limit, thereby minimizing pitting, arcing, and other maladies plaguing low frequency structures. Peak surface electric fields exhibited are less than about 160 MV/m.

Another object of the present invention is providing a tunable linear accelerator. A feature of the invention is that although the drift tube linac utilizes constant field permanent magnets, the voltage in the cavities and current in the magnets is scaled, depending on the charge-to-mass ratio of the beam. An advantage is that the entire system can be tuned to accommodate different types of beams (e.g., carbon ions and protons).

Briefly, the invention provides a method for accelerating protons and carbon ions up to 450 MeV/u in a very compact linac, the method comprising subjecting the particles to a radio frequency quadrupole field to accelerate the particles to at least about 3 MeV/u, a drift tube linac (DTL) to an energy of 20 MeV/u, followed by a coupled DTL to 45 MeV/u and finally a high-gradient section made of CCL-type standing wave cavities or negative harmonic traveling wave cavities operating at S-band frequencies and capable of delivering voltage gradients of 40 to 60 MV/m. Focusing the accelerated particles while accelerated to higher energy is provided by appropriately placed permanent magnets and electromagnetic quadrupoles.

The compactness and power efficiency of the linac is enabled by using high-gradient structure in the S-band frequencies for lower energy particles than ever before. The low-intensity required for hadron therapy allows the use of small-aperture S-band structures and the operation at very high gradient compared to high-intensity machines for research. Operating with very short sub-microsecond pulses at repetition rates up to 400 Hz allows the fast and flexible beam energy and intensity tuning not provided by existing hadron therapy machines. The designed linac is capable of accelerating ions (as heavy as neon ions) to the full 450 MeV/u energy, therefore allowing fast beam switching (e.g., between approximately 1 and 10 milliseconds) if different ion sources are installed in the front-end of the linac.

Also provided is a system for accelerating ions, the system comprising a radio frequency quadrupole capable of accelerating the ions to between approximately 1 MeV/u and approximately 5 MeV/u; a backward traveling wave drift tube linac positioned downstream of the quadrupole; and a wave structure capable of delivering a voltage gradient of about 45 MV/m to about 50 MV/m. The structure may be a standing or a traveling wave structure.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
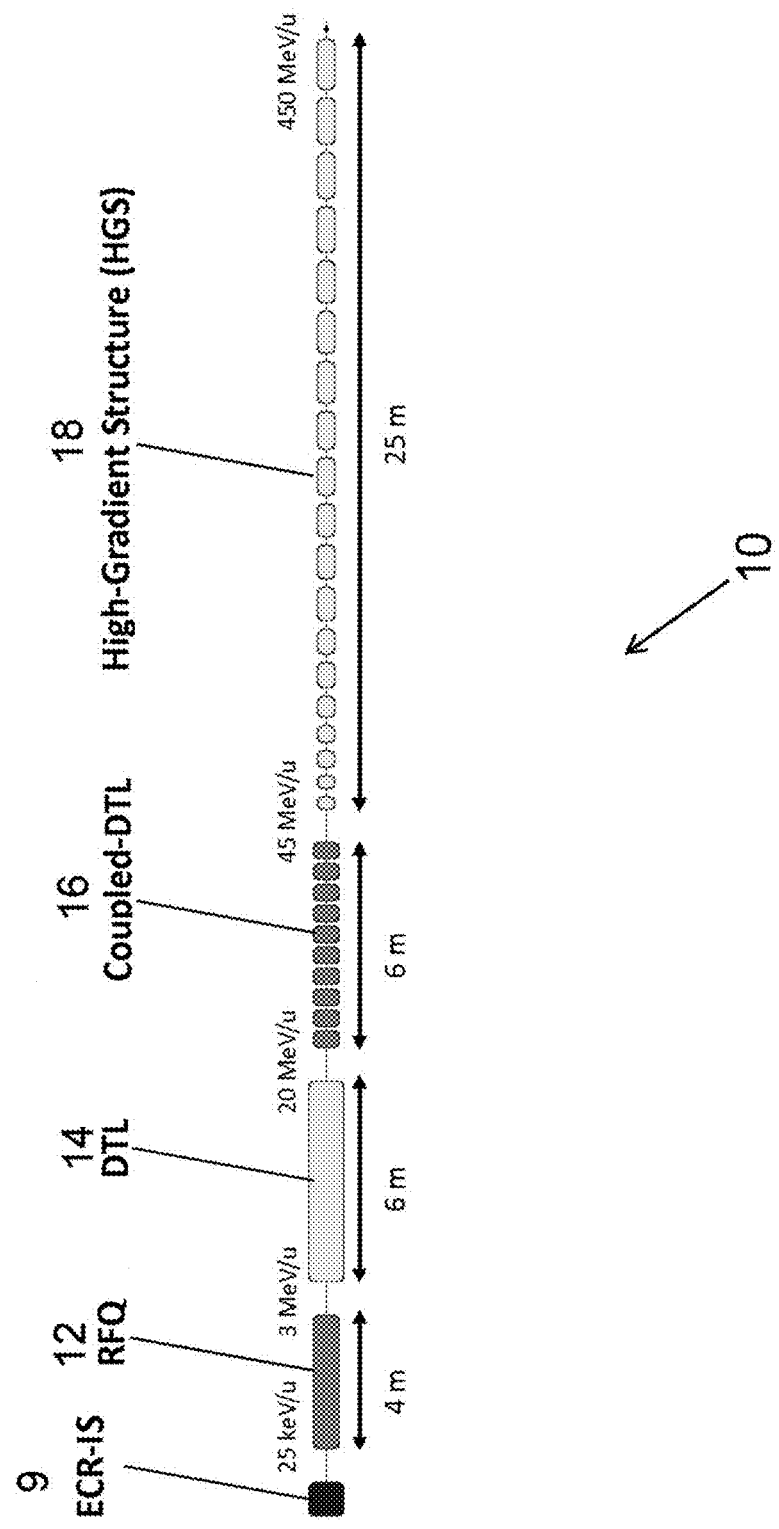
FIG. 1 is a schematic diagram of the linac system in accordance with features of the present invention.

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a compact, single-pass pulsed linear accelerator (linac) that uses high-gradient S-band structure. ("Single pass" is defined as the beam going through the accelerator once in contrast to a synchrotron where the beam makes thousands of turns to reach the desired energy.) This single pass feature enables the invented system to switch parts of the accelerator very quickly to adjust beam energy pulse-by-pulse, if necessary.

The invented linac is capable of adjusting the beam energy hundreds of times per second (e.g., from about 100

Hz to about 400 Hz). The repetition rate is defined as pulses per second. The energy (e.g. the pulse repetition rate) can be changed at 100 Hz or pulse per pulse if needed. The low energy feature of the system provides flexibility in beam tuning to enable fast and efficient 3D tumor scanning and multi-painting (whereby the volume of the tumor is exposed several times to the low energy beam, as opposed to only once by a very high, potentially damaging energy beam), as well as following the real-time motion of the tumor if needed (image guided therapy). By changing the pulse repetition rate, the beam intensity could be adjusted up to $10^{10}$ particles per second, and preferably between $10^8$ and $10^{10}$ particles per second. Typically $10^{10}$ protons or $10^9$ carbon ions are used The beam energy could be changed continuously up to the full energy of 450 MeV/u required to penetrate the depth of a human body, which is equivalent to about 30 cm of water. The flexibility in changing the energy quickly has to do with the linac being a single pass machine and the possibility to switch parts of the accelerator quickly to adjust the energy pulse by pulse if needed. This cannot be easily achieved in a synchrotron because of the multi-turn and cyclic nature of the machine.

The invented advanced ion linac is capable of accelerating a variety of ionized elements (up to neon) up to the full energy of 450 MeV/u. At this energy, ions lighter than carbon, including protons and helium ions, have ranges exceeding the width of the human body and could therefore be used for imaging purposes, as in proton tomography. It is also possible to deliver these beams with lower energies for treatment. Despite having ranges shorter than the human body, the system can use ions heavier than carbon (e.g. lighter than neon in the periodic table) for treatment at adjustable energies up to the full linac energy.

An embodiment of the invention comprises a linac design for a compact carbon, neon, proton accelerator that could be used for ion beam therapy and other applications. The invented system is capable of accelerating different ions to the same energy. As such, the invention allows variable-energy intensity-modulated therapy using multiple ion species.

An advanced compact carbon ion linac is provided, and depicted in FIG. 1 as numeral 10. The entire length of the invented system is depicted as 41 meters. As noted elsewhere herein, the length may vary from 30 to 45 meters.

The linac has the following main sections so as to fully leverage the fast change of beam velocity:
  A radio frequency quadrupole (RFQ) 12 which accelerates the beam to about 3 MeV/u. The RFQ operates at a sub-harmonic of the S-band frequency.
  A Drift Tube Linac (DTL) structure 14 to impart energy to the beam in a range from about 3 MeV/u to about 20 MeV/u.
  Coupled DTL structures 16 to impart energy to the beam in a range from about 20 MeV/u to 45 MeV/u.
  High gradient, standing or traveling wave structures 18 capable of delivering about 40 to about 60 MV/m so as to accelerate the beam to the full energy of 450 MeV/u in approximately 25 meters. This structure enables the compactness of the invented system. Use of negative harmonic cavities in this medium to high energy sections provides the highest power efficiency in this velocity range and allows for an overall reduction in power consumption. This accelerating structure is designed not for the fundamental harmonic m=0 but for the m=−1 harmonic. This makes the accelerating period longer which enhances power efficiency.

The front end accelerating structures such as the RFQ 12 and DTL 14 operate at lower frequencies to maintain high shunt impedance for low velocity ion beams. (Shunt impedance is the measure of power efficiency of a resonant radio frequency structure for charged particles acceleration.)

The invented linac system and method utilizes beam intensities (currents) that are five orders of magnitude less than those required of research linacs. With such high intensity beams not required, the invented system can operate with very short beam pulses (e.g., between about 100 and 2000 nanoseconds, preferably between about 200 and 800 nanoseconds, and most preferably between about 300 and 600 nanoseconds) in S-band frequencies ranging between about 2-4 GHz. This low intensity enables the use of smaller apertures and higher frequencies for the accelerating structures. Suitable aperture cross diameters range from about 2 to 12 mm, preferably 4-10 mm, and most preferably 6 to 8 mm. The smaller the aperture, the easier it is to produced higher fields. The larger the aperture, the better it is to let the beam pass through with minimal losses.

This invention's utilization of high frequencies and short RF pulses can provide ionized moieties (e.g., carbon, helium, protons) with any energy up to 450 MeV/u at 300 Hz repetition rates. The delivered beam intensity could also be adjusted by changing the pulse length and repetition rate (e.g., from about 100 to about 400 Hz). No energy degrader or energy selection system is necessary to provide the required treatment beam energy.

For short pulses, S-band accelerating structures can sustain about 160 MV/m peak surface electric fields without arcing or pitting occurring. Generally, the invention utilizes high-gradient accelerating structures, operating at voltage gradients of between 40 MV/m and 60 MV/m. Pulsed, room-temperature structures operating in the S-band frequency are capable of delivering such high gradients. For example, 35 MV/m real-estate accelerating gradients in this section result in a 35-meter long linac. This corresponds to about 1 GV of accelerating voltage for carbon ion beams.

Using different ion sources, a fast and effective multi-species variable-energy intensity-modulated ion beam therapy is enabled. Up to $10^{10}$ ions/sec can be delivered. Adjustable beam energy pulse-to-pulse, beam scan in all three dimensions (x,y,z) is enabled, thereby making three dimensional (3D) scanning of tumors straightforward and rapid.

The near 100 percent beam transmission through the linac allows the use of any suitable ion source 9 with the invention, such as for example the Dresden ECRIS-2.5M™ electron cyclotron resonance ion source, available from DREEBIT Ion Beam Technology, Dresden, Germany.

RFQ Detail

The invention uses a long (several wavelengths in length) high-frequency RFQ for initial acceleration of carbon beam to approximately 1 to 5 MeV/u. Suitable high frequency is about 476 MHz, which is a lower harmonic of the S-band.

Figure 2:
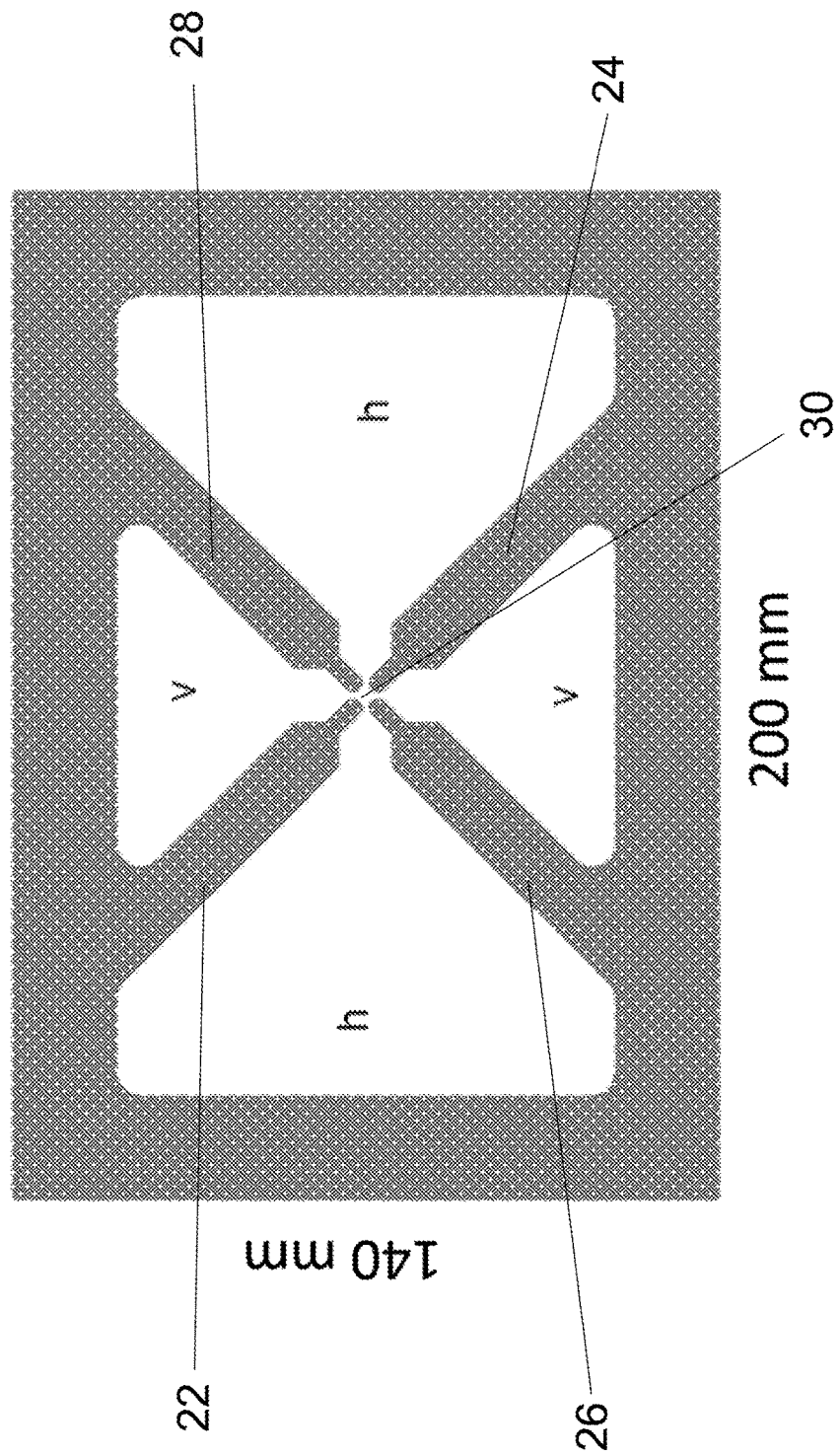
FIG. 2 is a cross section of an asymmetric four-vane RFQ, in accordance with features of the present invention.

The RFQ is based on an asymmetric 4-vane structure, as depicted in FIG. 2. FIG. 2 shows two horizontal voids or quadrants "h" opposing each other and two vertical voids "v" opposing each other. The cross sections of each of the quadrants are generally shaped as triangles, with their apices opposing each other at the center of the structure to define a center beam aperture 30. The sides of the triangles are inwardly projecting vanes, with the distal end of a first pair of vanes 22, 24 opposing each other and the distal ends of a second pair of vanes 26, 28 opposing each other, such that the distal ends all oppose each other to define the above mentioned center beam aperture. The horizontal voids h may be identical in void volume but different than the void volume of the vertically disposed voids v. This provides the asymmetry. Alternatively, there may be instances where either the horizontal voids or the vertical voids are not identical in volume to each other. The asymmetric four-vane structure provides good separation of non-operational modes. This allows for a long high frequency RFQ to generate a carbon beam.

In an embodiment of the RFQ, a first pair of vanes are provided such that a first vane 22 and a second vane 24 comprising the first pair diametrically oppose each other to form a gap. Further, a second pair of vanes orthogonally arranged to the first pair of vanes, but coplanar to the first pair of vanes, is similarly positioned such that a third vane and fourth vane comprising the second pair diametrically oppose each other. The distal ends of each of the vanes comprising the second pair similarly form the central gap. Together, the distal ends of the first and second vanes of the first pair of vanes and the distal ends of the third 26 and fourth 28 vanes of the second pair of vanes forms an aperture 30, adapted to receive a particle beam. As such, the aperture is coaxially arranged with the longitudinal axis formed by the RFQ.

The field stabilization in the RFQ is achieved by the above-described asymmetric quadrants. The non-symmetric quadrants provide a means for breaking or otherwise disrupting the symmetry for resonant modes other than the fundamental operating mode. FIG. 2 shows a rectangular RFQ cross section that is 140 mm in width and 200 mm in length, but these dimensions are illustrative only inasmuch as any dimensions suitable to achieve the desired field stabilization are suitable.

To avoid contamination from ion beams with Q/A=½, a $^{12}C^{5+}$ beam is extracted from the ion source, then stripped after its initial acceleration by the RFQ.

DTL Detail

Figure 3A:
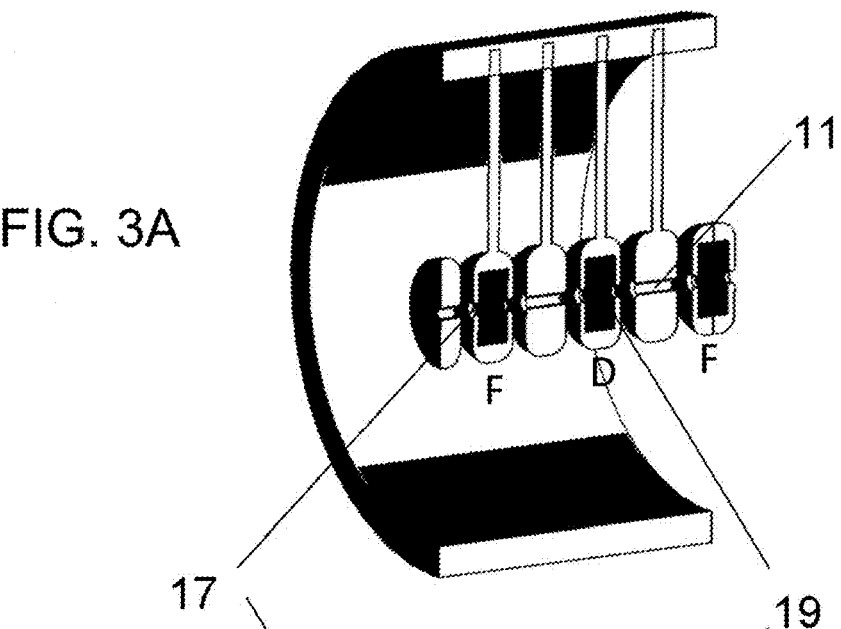
FIGS. 3A-D are various views of a drift tube linac (DTL) structure, in accordance with features of the present invention.
Figure 3B:
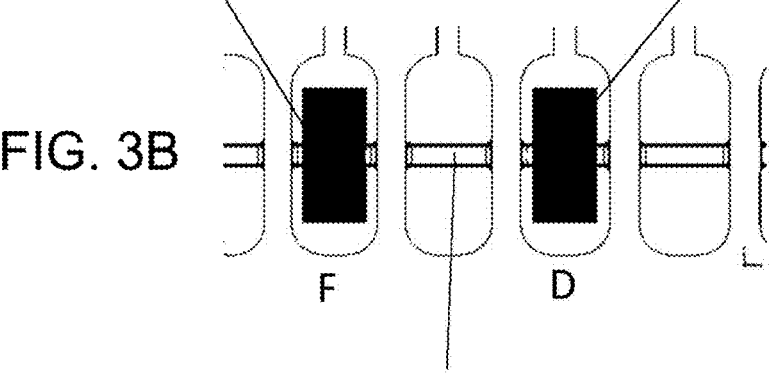
Figure 3C:
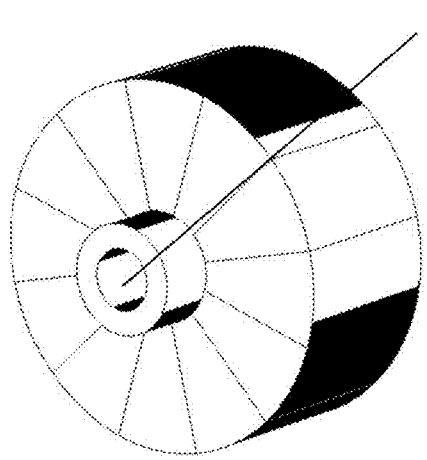

To provide both high efficiency and a high accelerating gradient, a TM-mode is preferred in the sections downstream of the RFQ. As depicted in FIGS. 3A-B, permanent magnets 17, 19 are installed in the serially arranged drift tubes for beam focusing. The beam line channel 11 is depicted in FIG. 3A-D. The drift tubes of the DTL are designed to house compact permanent magnet quadrupoles (PMQ).

For the sake of simplicity, two magnets are depicted, while in actuality, several magnets would be employed. A first magnet 17 may be arranged to provide focusing along the horizontal plane, while a second magnet 18 may be arranged downstream to provide defocusing along the horizontal plane. This defocusing is concomitant with focusing along the vertical plane. The use of permanent magnets adds to the compactness of the design. Despite the use of constant field permanent magnets, the focusing is kept stable for both protons and carbon.

Figure 3D:
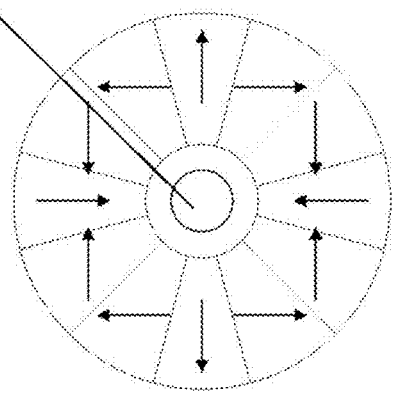

A 3D view of the designed segmented 12-piece NdFeB PMQ model is shown in FID. 3C. The arrows in FIG. 3D shows the orientation of magnetization of the 12 segments of the magnet.

The drift tube linac (DTL) structure 14 accommodates low energies from about 3 MeV/u to about 20 MeV/u. Both protons and carbons are accelerated in the same DTL with permanent magnets. Although the phase advance for proton and carbon beam is different, the transverse stability is provided for both beams. The beam matching is provided by a compact transition section from the RFQ to the DTL which includes compact electromagnetic lenses.

Coupled DTL
Section Detail

Due to the presence of small apertures, higher RF frequencies can be applied for the coupled DTL. The coupled DTL section has a frequency of 952 MHz and is made of coupled DTL tanks with electromagnetic quadrupole focusing in between. The coupled DTL section covers the energy range from 20 to 45 MeV/u. In the coupled DTL 16 depicted in FIG. 1, 10 tanks are shown, with 6 gaps per tank.

HGS Section
Detail

The application of HGS structures in the low energy section presented significant technical challenges due to high RF power losses and small geometrical dimensions of the accelerating cells of the coupled DTL section. Periodic structures have an infinite number of spatial harmonics. These harmonics have the same frequency but different spatial field distributions. Surprisingly and unexpectedly, these challenges were overcome by using a BWTW structure operating at the m=−1 spatial harmonic in this high gradient portion of the system. For example, a β of approximately 0.3 traveling wave negative harmonic cavity will lead to a much shorter linac than if only regular structures are used at higher β>0.4. Generally, the negative harmonic elongates the cell which eases the power dissipation and lowers the peak fields which consequently lowers the voltage breakdown rates.

In the high gradient structure 18 depicted in FIG. 1, 19 tanks are shown, capable of generating 2856 MHz pulse values.

Figure 5A:
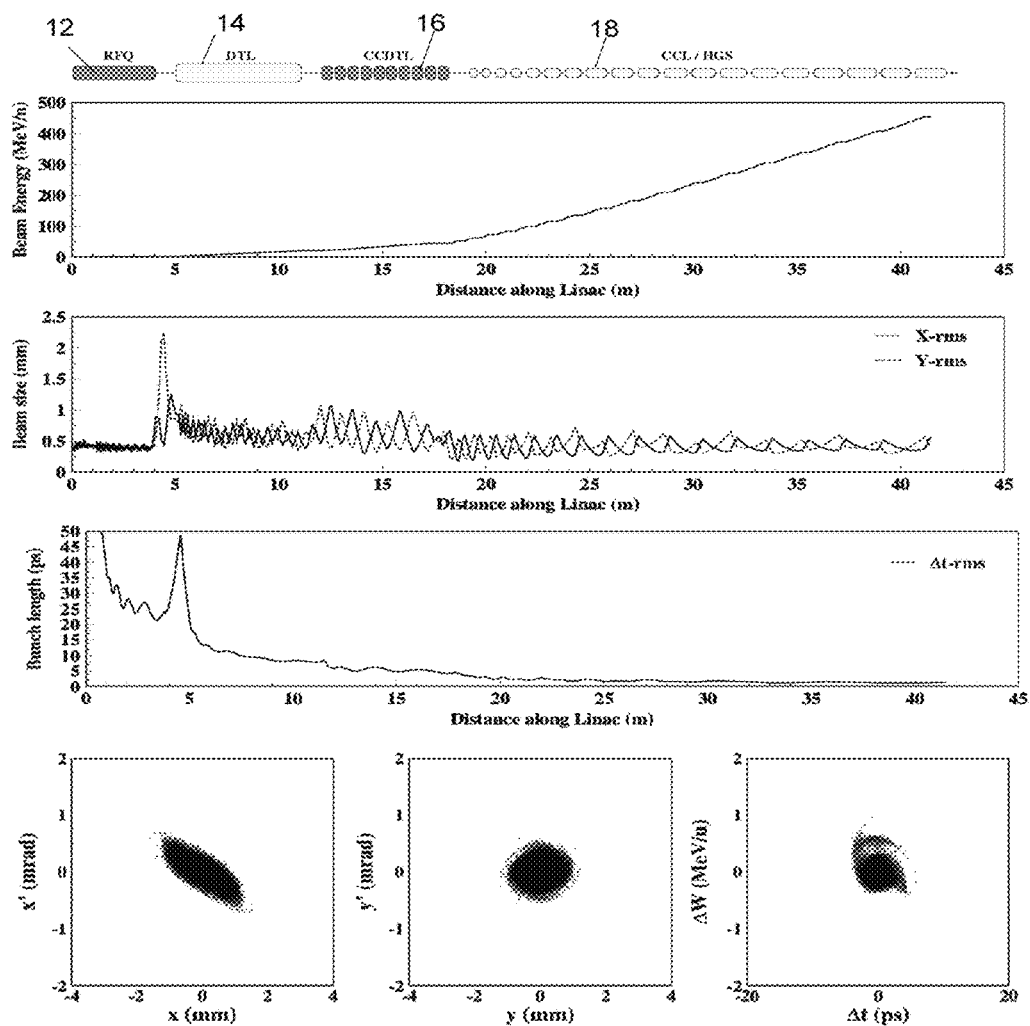
FIG. 5A is a depiction of carbon beam dynamics in the linac, in accordance with features of the present invention.

The beam dynamics for both carbon and proton beams generated by the invented system have been studied in detail using 3D field distributions for the accelerating structures and realistic initial beam distributions from the ion source. FIG. 5A depicts the results of carbon beam simulations using the TRACK code showing a smooth beam envelope along the linac in the bottom and good phase space distributions in the top.

The top three square-shaped plots show the 3-dimensional phase space occupied by the beam at the linac exit, exhibiting the desired and collected beam quality: 1) The first plot shows the horizontal position in mm in the horizontal axis and the horizontal angle in mrad in the vertical axis, 2) The second plot shows the vertical position in mm in the horizontal axis and the vertical angle in mrad in the vertical axis, 3) The third plot shows the time deviation in pico-second in the horizontal axis and the energy deviation in MeV/u in the vertical axis.

The middle rectangular shaped plot shows the transverse rms beam envelopes in mm along the linac from start to end. The bottom rectangular shaped plot shows the rms bunch width in pico-second (ps) along the linac.

The TRACK code is the beam dynamics code developed by Argonne National Laboratory, Lemont, Ill., and publically available therefrom, for example via https://www.phy.anl.gov/atlas/TRACK/ and other mirrors.

Figure 5B:
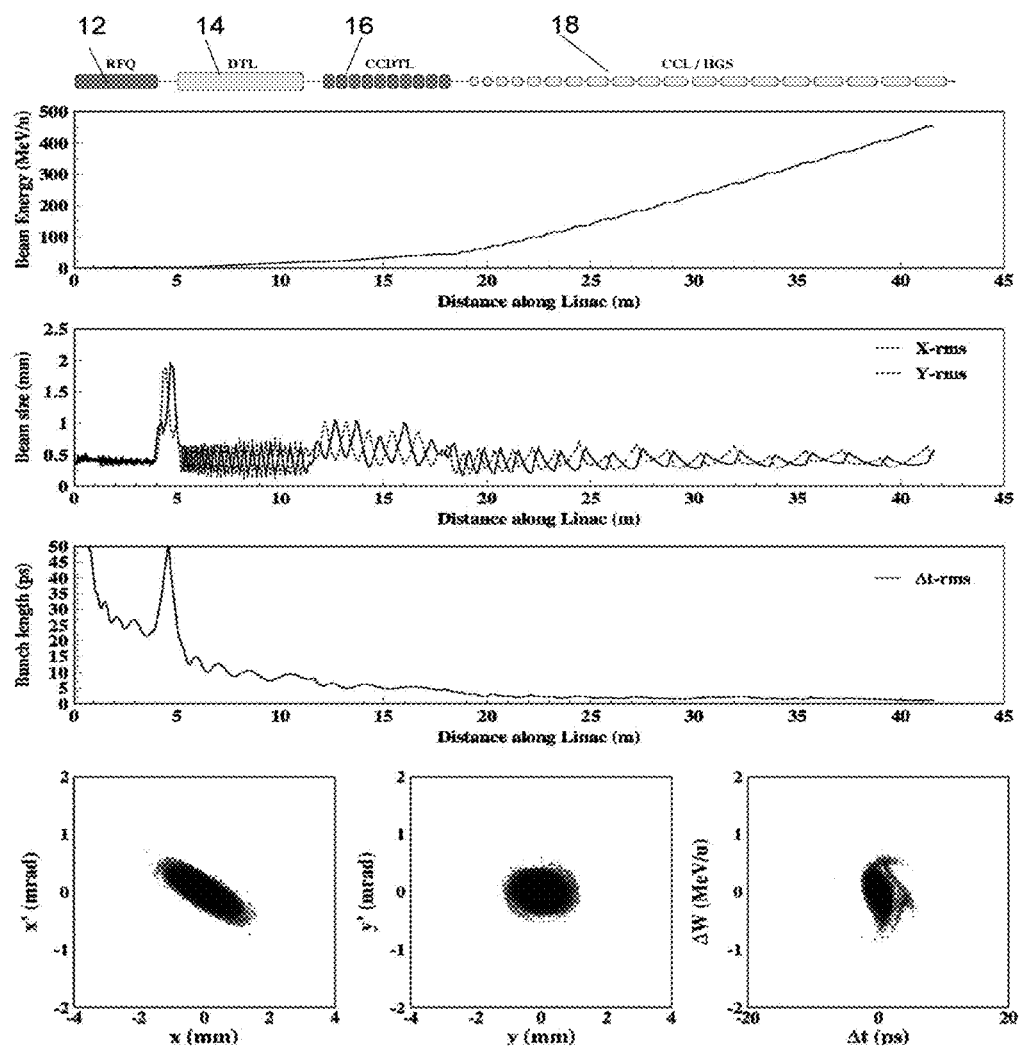
FIG. 5B is a depiction of proton beam dynamics in the linac, in accordance with features of the present invention.

These results confirm the feasibility of high-gradient acceleration while preserving good beam quality. Similar results were obtained for the proton beam by simple re-tuning of the linac. Those results are depicted in FIG. 5B. The data in FIG. 5B show that the invention can accommodate both proton beams and elemental ion beams. The content of the figure is similar to 5A but for proton beams. It shows that the linac is capable of producing good beam quality for both proton and carbon beams and any beam with the similar charge-to-mass ratio.

Typical radiation dose for hadron therapy is delivered at a rate of about $10^9$ carbon ions/second and about $10^{10}$ protons/second. This is achieved at a 120 Hz repetition rate, a beam pulse width below 0.5 micro seconds, and a pulsed electrical current of 13.3 micro Amps for $^{12}C^{5+}$ and 27 micro amps for protons. Commercially available Electron Cyclotron Resonance (ECR) ion sources, such as that identified supra, provide the required beam intensity for both $C^{5+}$ and protons. ($C^{6+}$ ions are preferred to avoid contamination by residual gas ions.)

The DC beam extracted from the ECR may be chopped into 100 to 600 nanosecond pulses (e.g., 0.5 micro second pulses), depending on the required beam intensity on the tumor. Typically, ECRs can provide carbon and proton beams with a normalized transverse emittance of 0.35 $\pi$·mm·mrad mrad containing 90 percent of the ions.

The invention provides a method and system for accelerating heavy ions up to 450 MeV/u. Features of the method and system include the use of low intensities, small apertures, short RF pulses, all in the high frequency (S-band) range. Use of high-gradient S-band structures in the high-energy section enables a compact linac. Concomitantly, the use of sub-harmonics structures in the low energy section provides the high shunt impedance, and low RF power consumption (low wall plug power) necessary for operation in space-restricted hospitals or university settings. The system can run at very high rep-rate (up to several hundred) at low cost.

The design was developed with nearly 100 percent transmission and a very high quality beam.

Adjustable beam energy pulse-to-pulse, beam scan in all 3 dimensions (x, y, z).

Acceleration of protons, fast switch between carbon and proton beams possible.

In summary, very compact room-temperature linear accelerator capable of delivering 450 MeV/u carbon ion beam or any other beam from protons to neon is provided herein. The invented design is the first full and most compact linac ever proposed for heavy-ion cancer therapy or any other application.

The invented linac has a smaller foot-print (about one half) and uses less power (about one fifth) than synchrotrons currently used for heavy-ion therapy, so as to make it possible for installation at a Hospital or University Campus. The compactness of the ACCIL linac is ensured by the use of high voltage-gradient accelerating structures up to 50 MV/m at lower energies than ever used before; as low as 45 MeV/u or a velocity v~0.3 c, where c is the speed of light.

Such a high accelerating gradient is made possible by combining the use of S-band frequency (~3 GHz) structures at very low duty cycles (<0.06%) with very short beam pulses (sub micro-seconds long), which significantly lowers the rf power requirements and the voltage break-down rates for low-cost and more reliable linac operations. Operations with very short beam pulses at very low duty cycles is possible due to the low beam intensity required for hadron therapy linacs compared to high-intensity linacs for research.

The invention's utilization of low-beam intensity allows a significantly low acceptance for the linac, making it possible to use very small apertures (~5 mm) and to use the more compact S-band frequency structures for acceleration.

Figure 6:
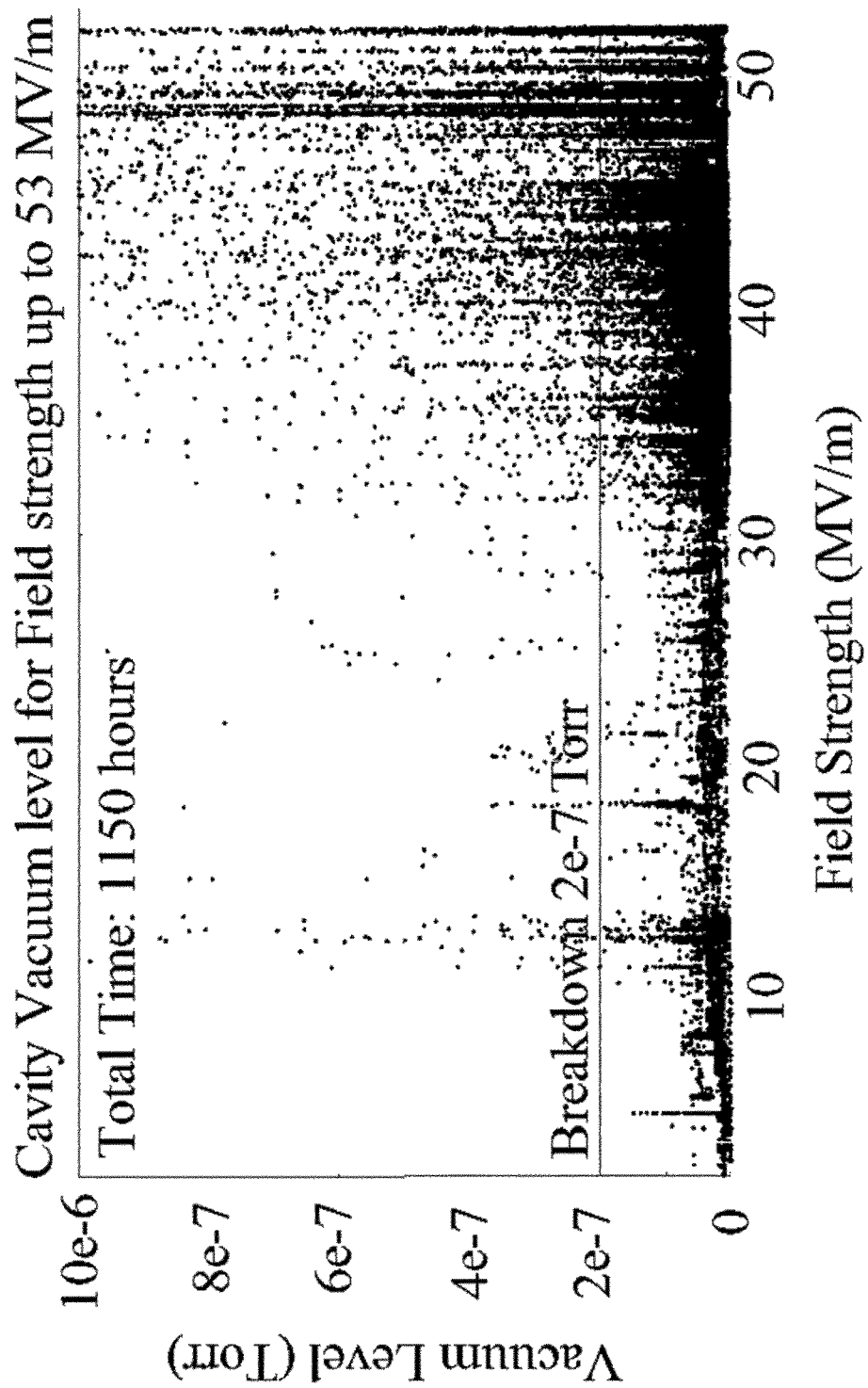
FIG. 6 is a depiction of high-power RF test results of a velocity of light (Beta+1, i.e. $\beta=1$) S-band accelerating structure achieving a voltage gradient of 52 MV/m, exceeding the requirements for the compact carbon ion linac, in accordance with features of the present invention.

The inventors demonstrated the highest gradient achieved on a velocity of light S-band structure of 52 MV/m with voltage breakdown rates below $10^{-6}$ per pulse. This structure was successfully operated at the same frequency and pulse structure required for the ACCIL linac, so as to prove the feasibility of the high-gradient required for the designed linac. FIG. 6. depicts the results of high-power RF tests for an S-band structure designed for electrons. This figure proves the feasibility of accelerating gradient as high as 52 MV/m at a frequency, pulse length and repetition rate similar to the requirements of the designed linac, so as to demonstrate that the requirements for the designed linac are achievable.

The invention represents the first application of traveling-wave negative harmonic cavities as the high-gradient structure in the low to medium velocity region starting from 45 MeV/u, or from 0.3 c to 0.7 c. This structure has the highest power efficiency in this velocity range and allowed us to shorten the linac and reduce its power consumption. Operating the S-band traveling-wave structures in the negative spatial harmonic mode expands the accelerating cell dimensions, which help power dissipation, reduce peak surface fields and lowers the voltage break-down rate.

The design of the low energy section of the linac, below 45 MeV/u, also has its innovative features due to possibility of using smaller apertures and higher frequencies than in modern hadron linacs for research.

Due to the fast change in beam velocity in the low-energy section of the linac, three different types of accelerating structures are used: a Radio Frequency Quadrupole (RFQ), a Drift Tube Linac (DTL) and a coupled DTL. The RFQ and DTL have their unique features. The RFQ is based on "asymmetric 4-vane structure". This feature is important to stabilize the structure and allows the use of a long high-frequency RFQ needed for carbon beam.

A new technique to accelerate both proton and carbon beams in the same DTL using permanent magnets is presented. Despite the different phase advance for proton and carbon, the transverse stability is provided for both beams. The matching between the RFQ and DTL is provided for both beams by a compact transition using tunable electromagnetic lenses.

Validation of high-gradient acceleration and efficient focusing for both carbon and proton beams using 3D beam dynamics simulations, so as to ensure that high-gradient acceleration is feasible while preserving the good beam quality. Following the RFQ, the beam transmission is close to 100%, this allows the use of commercial carbon ion sources. In contrast, the cyclotron-linac (cyclinac) combination proposed elsewhere, has very low beam transmission requiring high-intensity carbon sources, not commercially available.

In contrast to a synchrotron, the linac takes full advantage of the very low beam intensities required for hadron therapy. For the synchrotron, the machine dimension, cost and power consumption is defined by the magnet system. One needs to use the same magnets for low or high-intensity beams because the magnets size and power depends only on the beam energy.

Being a single pass pulsed machine, the ACCIL design allows fast energy change pulse per pulse up to 400 times per second, whereas, changing the beam energy in a synchrotron take one to few seconds. This linac feature allows fast depth scanning of the tumor by varying the energy. Similarly, it is possible to change the beam intensity by changing the number of pulses, from 100 to 400 pulses per second. Thus allowing intensity modulated painting of the tumor. Ultimately, different ion sources could be installed at the linac front-end and fast beam switching provided to allow the use of different ion beams in the same therapy session if needed.

In summary, an extremely compact room-temperature linear accelerator (ACCIL) has been developed, capable of delivering 450 MeV/u carbon ion beam or any other beam from protons to neon. The ACCIL design is the first and most compact linac proposed for heavy-ion cancer therapy or any other application. The conceptual design of the linac is fully developed including all accelerating structures and required beam focusing.

The invented ACCIL linac has a smaller foot-print (about one half) and uses less power (about one fifth) than synchrotrons currently used for heavy-ion therapy, so as to make it possible for installation at a Hospital or University Campus. The compactness of the ACCIL linac relies on the deployment of high-frequency (S-band) high-voltage structures in the medium to high energy section of the linac. The high voltage operation is possible because of the low-intensity requirement of a cancer therapy machine compared to high-intensity research linacs. The low beam intensity allows the operation with very short pulses at low duty cycle and high voltage of 50 MV/m with limited breakdown rates.

The inventors have demonstrated the highest voltage gradient of 52 MV/m, achieved on a velocity of light S-band structure with voltage breakdown rates below 10−6 per pulse. This structure was successfully operated at the same frequency and pulse structure required for the ACCIL linac, so as to proof the feasibility of the high-gradient required for the designed linac.

Traveling-wave negative harmonic cavities are utilized as the high-gradient structure in the low to medium velocity region starting from 45 MeV/u, or from 0.3 c to 0.7 c. This structure has the highest power efficiency in this velocity range and allowed us to shorten the linac and reduce its power consumption. Operating the S-band traveling-wave structures in the negative spatial harmonic mode expands the accelerating cell dimensions, which help power dissipation, reduce peak surface fields and lowers the voltage breakdown rate.

The design of the low energy section of the linac, below 45 MeV/u, also has its innovative features due to the possibility of using smaller apertures and higher frequencies than in modern hadron linacs for research. Due to the fast change in beam velocity in the low-energy section of the linac, three different types of accelerating structures are used: a Radio Frequency Quadrupole (RFQ), a Drift Tube Linac (DTL) and a coupled DTL. The RFQ and DTL have their unique features.

The RFQ is based on "asymmetric 4-vane structure". This feature is important to stabilize the structure and allows the use of a long high-frequency RFQ needed for carbon beam.

For the DTL, the inventors developed a new technique to accelerate both proton and carbon beams in the same DTL using permanent magnets. Despite the different phase advance for proton and carbon, the transverse stability is provided for both beams. The matching between the RFQ and DTL is provided for both beams by a compact transition using tunable electromagnetic lenses.

Validation of high-gradient acceleration and efficient focusing for both carbon and proton beams using 3D beam dynamics simulations, so as to ensure that high-gradient acceleration is feasible while preserving the good beam quality.

The linac beam transmission from the source to the target is close to 100 percent allowing the use of commercially available ECR ions sources. Also, for carbon beam and to avoid contamination from gas ions, C5+ is extracted and first accelerated through the RFQ before being stripped to C6+ and accelerated through the rest of the linac.

Being a single pass machine, the linac design allows fast beam energy change by turning on and off the last accelerating modules. Its pulsed nature allows modulation of the beam intensity by simply changing the pulse repetition rate. Also, if different ion sources were installed at the front-end, fast switching of beam species could be realized. Therefore, energy and intensity modulated treatment could be performed using multi-ion species if needed.

Except for the focusing in the DTL which uses constant-field permanent magnets, the rest of the linac is simply re-tuned from proton to carbon, for example, by scaling the voltages in the accelerating cavities including the RFQ and the current in the focusing electromagnets by a factor of two, which is the mass-to-charge ratio of carbon to proton. The inventors have determined that the different ions will have the same velocity at the same point of the linac which is why scaling works. Arrival times and energy gains in accelerating cavities will be the same and the focusing in the magnets will depend only on the magnetic field, the latter of which scales linearly with the current.

For the DTL however, the voltage is scaled by the mass-to-charge ratio but the permanent magnets are non-tunable, therefore the focusing is different between proton and carbon. A measure of the focusing is the transverse phase advance which is the beam rotation angle in the phase space. This phase advance will be different for proton and carbon beams, but in the instant system, the permanent magnets are designed to provide stable motion for both beams by keeping the phase advance below 90 degrees per focusing period. For matching to and from the DTL, tunable electromagnets are used in the transition sections.

Up to $10^{10}$ carbon ions per second can be delivered having a variable energy of from about 45 MeV/u to about 450 MeV/u. To achieve the accelerating gradients short pulses (approximately 500 ns), flattop, were utilized. (Flat top describes a uniform beam distribution in time during the pulse, then zero beam outside the pulse.)

A four vane RFQ, a transverse cross section of which is as shown as numeral 20 in FIG. 2, accelerates a $^{12}C^{5+}$ ion beam to 3 MeV/u over a length L of 4 meters.

The RFQ operating frequency f=476 MHz provides a suitable accelerating gradient, moderate field sensitivity to local random errors of resonator geometry, which scales as $(f \cdot L)^2$ and sufficient beam acceptance. (L is the length of the RFQ.)

Downstream of the RFQ, the $C^{5+}$ beam is converted to $C^{6+}$ by stripping with a thin carbon foil, wherein the beam passes through the foil. Suitable thicknesses are between about 10 and about 100 μg/cm$^2$.

A suitable TM-mode structure in the 3-20 MeV/u energy range is a multi-gap DTL (commercially available from The Institute of Applied Physics (IAP), Goethe University Frankfurt, Germany. For example, a 65-aperture (also known as gap), 476 MHz DTL provides acceleration and focusing for both fully stripped carbon ion and proton beams.

As depicted in FIGS. 3A-D, a focusing-defocusing (FODO) lattice is provided by compact 140 T/m permanent quadrupole magnets. (Typically, a FODO lattice comprises a focusing quadrupole, a field-free drift space, a defocusing quadrupole, and another drift space.) The average electric field of $E_0$=81.6 MV/m, and the accelerating gradient of $E_0T$=6.58 MV/m for carbon beam remain constant along the 6-meter DTL section.

To reduce construction cost and keep the accelerating gradient high, up to 12 MV/m, 10 coupled 6-gap DTLs operating at 952 MHz are employed up to 45 MeV/u. The FODO lattice is provided by compact 90 T/m electromagnetic quadrupoles located between the tanks. (Each tank consists of 6 equal cells and the synchronous phase is $\Phi_s=-90°$. The RF phase of the beam center slips around the reference phase $\Phi_r$, which is defined as an average RF phase of the beam center in the whole tank.

S-band structures for the main section 16 of the system can be composed either from standing wave or travelling wave mode structures. The standing wave configuration comprises 19 tanks of coupled cavities (known as coupled cavity linac or CCL) with electromagnetic focusing quadrupole doublets between them to cover the energy range of 45 to 450 MeV/u. Each CCL tank consists of several identical cells, for example from 20 to 36 cells per tank, and provides 50 MV/m accelerating gradient.

Figure 4:
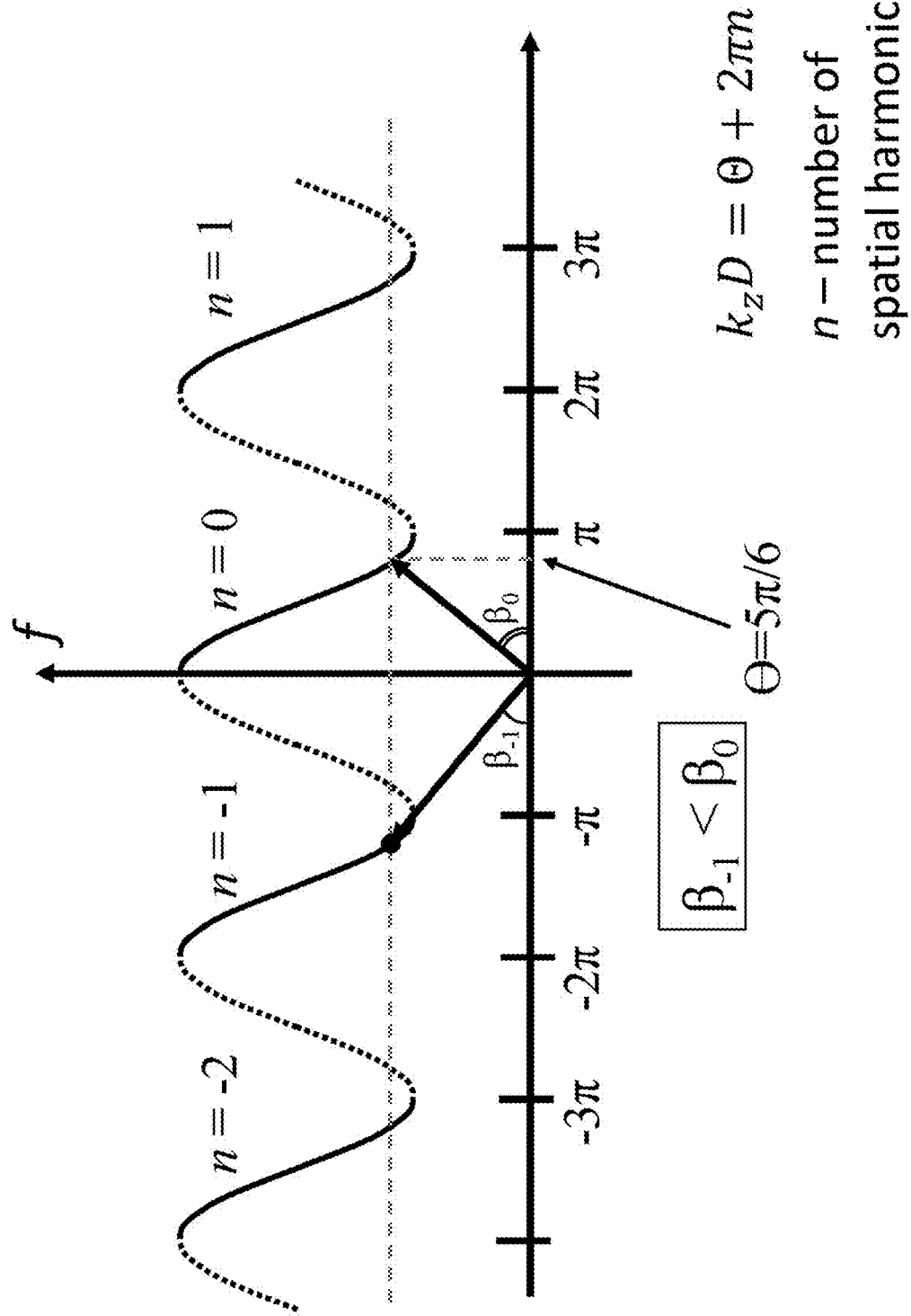
FIG. 4 is a dispersion diagram for periodic structure with magnetic coupling holes, in accordance with features of the present invention.

The performance of the S-band accelerating structures in the velocity range of 0.3 to 0.5 c is improved if a negative spatial harmonic of the traveling wave type is used. The negative harmonic provides a longer acceleration cell, as depicted by the left angled arrow in FIG. 4, compared to the right angled arrow. Such increased length results in less heat generation, and provides greater efficiency.

FIG. 4 depicts that a $5\pi/6$-mode traveling wave structure for $\beta_{-1}=0.3$ for acceleration by the negative first spatial harmonic was utilized). This structure has a cell length corresponding to $\beta_0=0.42$ and therefore improves the overall efficiency. This structure allows for the application of iris noses. The geometry of the traveling wave structure was optimized inasmuch as they are designed not for the fundamental harmonic m=0, but for the m=−1 harmonic, which makes the accelerating period longer. This results in both maximum efficiency for $\beta=0.3$ ion beam and reduced peak electric and magnetic fields. Surprisingly and unexpectedly, there are not focusing or defocusing effects from the fundamental harmonic of the electromagnetic field.

Pulse-to-pulse beam energy adjustment occurs by turning off portions of the CCL tanks or equivalent high-gradient structures, thereby providing for efficient 3D tumor painting.

The S-band section represents approximately half the linac length and consumes about 85 percent of power to the system. Increasing the effective shunt impedance of the S-band accelerating structures or reducing the real-estate accelerating gradient could reduce power consumption by half.

Example

A compact (8×45 meters) Advanced Compact Carbon Ion Linac was developed, capable of providing 50 MV/m for particles with a beta of from about 0.3 to about 0.7. The high operating gradients are enabled by operation at high frequency (e.g., 2856 MHz), at very low duty cycle (e.g., less than 0.06 percent) and for very short (less than 0.5 microsecond) beam pulses. The duty cycle is the product of the pulse length multiplied by the repetition rate, so one may have a relatively long pulse at a very low repetition rate.

Since all ion species will have the same velocity or energy per nucleon at any given point in the linac, a specific example of the carbon beam is provided here. The results shown in FIG. 5A were obtained using the beam dynamics code TRACK, locally developed at ANL. The sequence of the beam line element as well as their appropriate voltage and current settings are used as input to the code.

The $^{12}C^{5+}$ beam is extracted from the ion source (not shown) and injected into the RFQ 12 (first element on the linac layout at the top of FIG. 5A) at 25 keV/n (kilo electron-volt per nucleon). Then the beam is accelerated inside the RFQ to an energy of 3 MeV/n (Mega electron-volt per nucleon). The first plot in FIG. 5A displays the beam energy as the beam travels through the entire invented system.

At the exit of the RFQ, the $^{12}C^{5+}$ is stripped from its only electron to produce a $^{12}C^{6+}$ beam which is injected into the DTL 14 at about 3 MeV/n. The beam is then accelerated in the DTL to an energy of 20 MeV/u.

Upon exiting the DTL 14, the beam enters the coupled DTL structures (CCDTL) 16. The CCDTL 16 imparts an energy of 45 MeV/n to the beam, corresponding a linac length of about 20 meters.

The last acceleration phase is the CCL 18 or the high-gradient structure which is only about 25 meters long but will multiply the beam energy by a factor of 10 to 450 MeV/n. The second plot shows the rms beam size in mm along the linac in both the horizontal and vertical planes. The third plot shows the bunch length in pico-second. The beam size remains below 1 mm while the bunch length shrinks from about 50 pico-seconds to under 2 pico-second.

At the bottom of FIG. 5A is the final output of the simulation which shows how the beam looks like in the three phase planes at the linac exit. These three square-shaped plots show the 3-dimensional phase space occupied by the beam at the linac exit, exhibiting the desired and collected beam quality: 1) The first plot shows the horizontal position in mm in the horizontal axis and the horizontal angle in mrad in the vertical axis, 2) The second plot shows the vertical position in mm in the horizontal axis and the vertical angle in mrad in the vertical axis, 3) The third plot shows the time deviation in pico-second in the horizontal axis and the energy deviation in MeV/u in the vertical axis.

In the simulation code TRACK, the retuning from carbon to proton for example is done simply by scaling the settings of the beam line elements. The input to the code such as voltage and current settings are scaled down by a factor of two to account for the mass-to-charge ratio of the two beams. In this case the results are shown in FIG. 5 B for the proton, showing very similar beam dynamics as the carbon beam. In the real machine, the scaling is done through the software that controls the machine, which can be done within seconds or less, depending mainly on the response of the beam line elements.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A method for accelerating charged particles, the method comprising
   a) subjecting the particles to a radio frequency quadrupole field for a time sufficient to accelerate the particles to 1-3 MeV/u;
   b) focusing the accelerated particles; and
   c) increasing the energy of the accelerated particles to 45-450 MeV/u by imparting energy to the focused accelerated particles.

2. The method as recited in claim 1 wherein the particles are $^{12}C^{+5}$ and the particles are converted to $^{12}C^{+6}$ upon leaving the radio frequency quadrupole.

3. The method as recited in claim 1 wherein the step of focusing the accelerated particles comprises subjecting the accelerated particles to a drift tube linac operating at a sub-harmonic of the S-band frequency.

4. The method as recited in claim 1 wherein the step of focusing the accelerated particles comprises accelerating the particles to up to approximately 45 MeV/u.

5. The method as recited in claim 1 wherein imparting energy comprises subjecting the focused accelerated particles to a voltage gradient of between 40 MV/m and 60 MV/m.

6. The method as recited in claim 1 wherein imparting energy comprises subjecting the focused accelerated particles to radio frequency pulses.

7. The method as recited in claim 6 wherein the radio frequency pulses are between 100 nanoseconds and 1000 nanoseconds in duration.

8. The method as recited in 6 wherein the pulse repetition rate is from 100 Hz to 400 Hz.

9. The method as recited in claim 1 wherein the focusing step further comprises subjecting the particles to an acceleration cell that utilizes the negative first spatial harmonic of the wave.

10. A system for accelerating ions, the system comprising:
    a) a radio frequency quadrupole capable of accelerating the ions to between 1 MeV/u and 5 MeV/u;
    b) a drift tube linac positioned downstream of the quadrupole; and
    c) a wave structure capable of delivering a voltage gradient of 40 MV/m to 60 MV/m.

11. The system as recited in claim 10 wherein the ions are protons, or charged elements having an atomic weight less than neon.

12. The system as recited in claim 10 wherein the drift tube linac operates at a sub-harmonic of the S-band frequency.

13. The system as recited in claim 10 wherein the drift tube linac accelerates the ions to up to approximately 45 MeV/u.

14. The system as recited in claim 10 further comprising a means for stripping electrons from the ions, wherein the means resides downstream of the quadrupole.

15. The system as recited in claim 10 wherein the quadrupole comprises a plurality of vanes defining a center aperture adapted to receive a beam of the ions.

16. The system as recited in claim 10 wherein the quadrupole comprises a plurality of vanes asymmetrically arranged relative to each other and coplanar with each other.

17. The system as recited in claim 10 wherein both proton and ion beams are produced using tunable electromagnetic magnets.

18. The system as recited in claim 11 wherein the drift tube linac is immersed in a magnetic field produced by a constant field permanent magnet.

* * * * *

UNITED STATES PATENT AND TRADEMARK OFFICE
CERTIFICATE OF CORRECTION

PATENT NO. : 10,362,666 B2
APPLICATION NO. : 15/713238
DATED : July 23, 2019
INVENTOR(S) : Brahim Mustapha et al.

Page 1 of 1

It is certified that error appears in the above-identified patent and that said Letters Patent is hereby corrected as shown below:

On the Title Page

Item (54) and in the Specification Column 1 Line 1, change "COMPAC CARBON ION LINAC" to "COMPACT CARBON ION LINAC"

Signed and Sealed this
Twenty-second Day of September, 2020

Andrei Iancu
*Director of the United States Patent and Trademark Office*